United States Patent [19]
Barnea

[11] Patent Number: 6,162,188
[45] Date of Patent: Dec. 19, 2000

[54] PENILE TUMESCENCE AND RIGIDITY MONITORING DEVICE

[75] Inventor: Ofer Barnea, Herzliya, Israel

[73] Assignee: Meduck Ltd., Tel Aviv, Israel

[21] Appl. No.: 09/374,628

[22] Filed: Aug. 16, 1999

[51] Int. Cl.$^7$ .................................................. A61B 5/103
[52] U.S. Cl. ............................................................ 600/587
[58] Field of Search ..................................... 600/587, 504, 600/38, 39, 40, 41

[56] References Cited

U.S. PATENT DOCUMENTS

| | | | |
|---|---|---|---|
| 4,169,463 | 10/1979 | Piquard | 600/504 |
| 4,469,108 | 9/1984 | Goldstein | 600/504 |
| 4,474,187 | 10/1984 | Timm et al. | 600/587 |
| 4,913,162 | 4/1990 | Leang et al. | 600/587 |
| 4,928,706 | 5/1990 | Trick | 600/587 |
| 5,692,520 | 12/1997 | Lavoisier | 600/587 |

Primary Examiner—Cary O'Connor
Assistant Examiner—Pamela Wingood
Attorney, Agent, or Firm—Mark M. Friedman

[57] ABSTRACT

A method and device for measuring nocturnal penile tumescence and rigidity. In a first embodiment, two circular elastic sensors of differing viscoelasticities, placed around a penis, sense changes in penile circumference, which describes penile tumescence. A comparison of the instantaneous circumferences of the two sensors describes penile rigidity. Sensor circumference is measured by monitoring changes in electrical resistance across the sensor. In a second embodiment, a single circular elastic sensor senses changes in penile circumference (describing tumescence), while rigidity is described by changes in amplitude of a plethysmographic signal sensed by the single circular sensor. In a third embodiment, a photoplethysmographic sensor senses a penile plethysmographic signal. The signal mean intensity describes penile tumescence, and changes in amplitude of the plethysmographic signal describe changes in cardiac outlook.

24 Claims, 6 Drawing Sheets

PENILE TUMESCENCE AND RIGIDITY MONITORING DEVICE

FIELD AND BACKGROUND OF THE INVENTION

The present invention relates to the evaluation of male sexual dysfunction and, in particular, it concerns a method and device for evaluating the occurrence of nocturnal penile erection in a male suffering from impotence.

Impotence, or male erectile dysfunction (ED), is defined as the inability to achieve or maintain an erection adequate for the performance of sexual intercourse. Erectile dysfunction impairs sexual performance, diminishes self-(esteem and disrupts personal relationships. It affects approximately 10–20 million men in the US according to the NIH Consensus Development Panel on impotence (JAMA 1993, 270:83–90).

For a penile erection to be adequate for the performance of sexual intercourse it is necessary that the erect penis be both adequately tumescent (that is, enlarged and swollen relative to it's flaccid state) and adequately rigid. The process of penile erection occurs in several phases:
1. During the initial, flaccid, phase the volume of the penile erectile tissue (the corpus cavenosum) is small (approximately 20% of maximum volume) and the corporal al pressure is low (approximately 20 mmHg).
2. During the tumescent, or filling, phase a reduction in alpha-sympathetic tone results in dilation of the penile arteries and constriction of the penile veins, thus allowing arterial blood to build up in the corpus cavenosum. This causes the corporeal pressure to rise, pressing the penile veins against the surrounding tunica and further increasing the hemodynamic resistance to venous outflow. As the intra-corporeal pressure approaches systolic levels (100 mmHg), the volume of the penile erectile tissue grows by approximately 80%.
3. During the rigid phase, contraction of the perineal muscles and the pressure of the corpus cavernosum against the taut surrounding fibrous coats result in the rigidity required for full erection.
4. The phase of detumescence begins with contraction of the penile arteries, thus restricting arterial inflow, and reopening of venous drainage from the erectile tissue. This causes corporal volume and pressure to gradually return to flaccid levels.

Tumescence is thus controlled by the autonomic nervous system, which regulates blood flow to the penis, while rigidity is related to the pressure-volume relationship of the tumescent erectile tissue and it's surrounding fibrous fascia, and is also influenced by local muscle tone. As tumescence that is not followed by sufficient rigidity does not result in a functional erection, both these phase of penile erection should be evaluated when assessing male sexual dysfunction. Tumescence monitoring alone, therefore, without a concomitant assessment of penile rigidity, allows for only a limited description of erectile function (Levine LA and Lenting EL,. Use of Nocturnal penile tumescence and rigidity in the evaluation of male erectile dysfunction. Urol Clin North Am 1995 Nov;22(4):775–788).

During sleep, normal fluctuations in autonomic neural tone result in periodic, transient penile erections. When erectile dysfunction is of psychological origin, these nocturnal erections are unaffected. However, when dysfunction is organic in nature, an absence of nocturnal penile tumescence and rigidity (NPTR) can be expected. Thus, to assess whether male sexual dysfunction due to inadequate penile tumescence and/or rigidity is organic or psychogenic in origin, it is necessary to monitor the patient for the occurrence of penile tumescence and rigidity during sleep.

Several methods and devices for measuring nocturnal tumescence have been described. Thus, strain gauges installed on elastic bands (U.S. Pat. No. 4,572,211 and U.S. Pat. No. 4,700,715), or on silicon rings filled with mercury (U.S. Pat. No. 4,103,678 to Karacan) have been used to passively measure nocturnal changes in penile circumference (indicating the occurrence of tumescence). These devices suffer from the deficiency that they provide no measurement of penile rigidity. Furthermore, the mercury within the device of Karacan is a hazardous substance, which may induce toxic effects if it leaks from the silicon ring and comes into contact with the patient's skin.

A device for passively measuring penile rigidity (the occurrence of which implies that tumescence must have occurred as well) has been described by Timm in U.S. Pat. Nos. 4,474,187, 4,766,909, and 4,911,176. In this device, a wire surrounding the penis snaps at a predetermined force, thus indicating that penile rigidity has surpassed a predetermined level. This device suffers from the deficiency that the measurement of rigidity is not quantitative, thus precluding an assessment the number and timing of episodes of erection during the course of a nocturnal study. Goldstein (U.S. Pat. No. 4,469,108) described a mechanical, manually operated device for measuring penile rigidity. This device is thus unable to automatically monitor rigidity during sleep.

Timm (U.S. Pat. Nos. 4,515,166 and 4,848,361) described a device capable of actively measuring both tumescence and rigidity (the "Rigiscan", Dacomed Corporation, Minnesota, USA). This device utilizes electrical torque motors to apply tension to a wire ending in a loop placed on the penis. The motor applies an intermittent force, every 15 to 30 seconds, to the wire, which forms a slipknot loop around the penis. Shortening of the wire loop is measured with each application of torque. When the penis is fully rigid and unyielding, the wire will not shorten at all, while lesser degrees of rigidity will result in variable degrees of shortening of the wire.

Although this device allows for the automatic measurement of both tumescence (indicated by a progressively enlarging wire loop) and rigidity (indicated by progressively lesser degrees of wire shortening in response to torque), the Rigiscan suffers from the deficiency that it measures these parameters by active means, that is, force or pressure on the penis is actively generated so as to measure the compliance of the penile tissue. This procedure is uncomfortable and disturbing for the patient. Furthermore, the force generating elements (two torque motors) are large and unwieldy, making such devices cumbersome for the patient to wear while sleeping (measuring approximately 21 cm by 5 cm and weighing over 1.5 Kg). Indeed, the Rigiscan causes such discomfort when attached to the patients thigh that it is necessary to attach the device to the patient on two consecutive nights prior to performing the study, so as to accustom the user to sleeping with a heavy device attached to his thigh.

Lavoisier described a device for actively measuring rigidity by measuring the water pressure in a rigid cuff surrounding the penis (U.S. Pat. Nos. 4,747,415, and 5,692,520). Trick (U.S. Pat. No. 4,928,706) described a device in which the flow of water from one cuff surrounding the penis into a second, connected cuff is used to quantify the degree of tumescence, and displacement of an active sensor in the second cuff is used to determine rigidity. Both these devices utilize fluid filled cuffs placed around the penis and achieve their measurements by active means. They thus suffer from the same deficiencies as described above for the Rigiscan.

There is therefore a need for, and it would be highly advantageous to have, a single device capable of automatically measuring both penile tumescence and penile rigidity by passive means. Such a device should be sufficiently small and lightweight as to be comfortable for the user to wear, and thus not disturb the users sleep. Furthermore, the passive means used to measure penile tumescence and rigidity should not cause pain or discomfort to the user, and the device should be safe to wear, with no risk of exposure to noxious substances involved.

SUMMARY OF THE INVENTION

The current invention is a method and device for measuring both penile tumescence and rigidity in a passive manner.

In a first embodiment of the device, two elastic bands of differing elasticity, or two fluid-filled tubes of differing elasticity, are placed adjacently to each other on the shaft of the penis and serve as sensors of penile circumference. Changes in circumference of the sensors are monitored by measuring changes in electrical resistance across an electrically conductive material contained within the sensors. A standard computer processor analyzes the sensor output, using changes in sensor circumference to describe penile tumescence, and a comparison of the instantaneous circumferences of the two sensors to describe penile rigidity.

In a second embodiment of the current invention, a single sensor (being either a conductive elastic band or a conductive fluid-filled tube, as used in the first embodiment of the invention) is placed around the shaft of the penis and senses a plethysmographic signal. A standard computer processor analyzes the acquired plethysmographic signal, using changes in mean signal intensity to describe penile tumescence, and changes in signal amplitude relative to changes in tumescence to describe penile rigidity.

In a third embodiment of the current invention a single reflective photoplethysmographic sensor is placed around the shaft of the penis and senses a plethysmographic signal. A standard computer processor analyzes the acquired plethysmographic signal, using changes in mean signal intensity to describe penile tumescence, and changes in signal amplitude relative to changes in tumescence to describe penile rigidity It will be understood that combinations of these three, embodiments are possible, using, for example, an elastic band sensor to measure tumescence by means of changes in sensor circumference, and a photoplethysmographic sensor to measure rigidity at the same time. In all embodiments, the small and lightweight sensors are the only components of the device that come into contact with the patient. The sensors are connected to a resistance-measuring device and a small data-logger such as the A-ENGINE-P (TERN INC., Davis, Calif., USA). The data is downloaded to a computer processor either directly by cable, or via telemetry. When the sensor is a photoplethysmograph, however, the sensor output does not pass through a resistance-measuring device. Rather, the sensor output is directly input to an electronic circuit that generates a signal that is proportional to the amplitude of the pulse detected by the photoplethysmograph (amplitude demodulation). According to the teachings of the present invention there is provided a method for measuring the rigidity of a penis, including positioning a first circular sensor and a second circular sensor around the penis, the first and second circular sensors each being of different viscoelasticity to each other; measuring a circumference of the first circular sensor and a circumference of the second circular sensor; and calculating a comparator of the measured circumferences of the first and second circular sensors. There is further provided a method for measuring erectile function of a penis, including sensing a plethysmographic signal from the penis, the plethysmographic signal depicting pulsatory changes in the penile volume over time; and measuring a mean intensity of the sensed plethysmographic signal. There is. further provided a system for measuring rigidity of a penis, including a first circular sensor, operative to increase in diameter in response to an increase in diameter of the penis; a second circular sensor, operative to increase in diameter in response to an increase in diameter of the penis, the second circular sensor being of different viscoelasticity to the first circular sensor; a mechanism for measuring a circumference of each of the circular sensors; and a processor for calculating a comparator of the measured circumferences of each of the circular sensors. There is further provided a system for measuring erectile function of a penis, including a plethysmographic sensor, operable to sense a plethysmographic signal from the penis; and a processor, operable to process the sensed plethysmographic signal so as to describe a change in mean signal intensity.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a device and method for the passive measurement of penile tumescence and rigidity.

The principles and operation of a device and method for the passive measurement of penile tumescence and rigidity, according to the present invention, may be better understood with reference to the drawings and the accompanying description.

Figure 1:
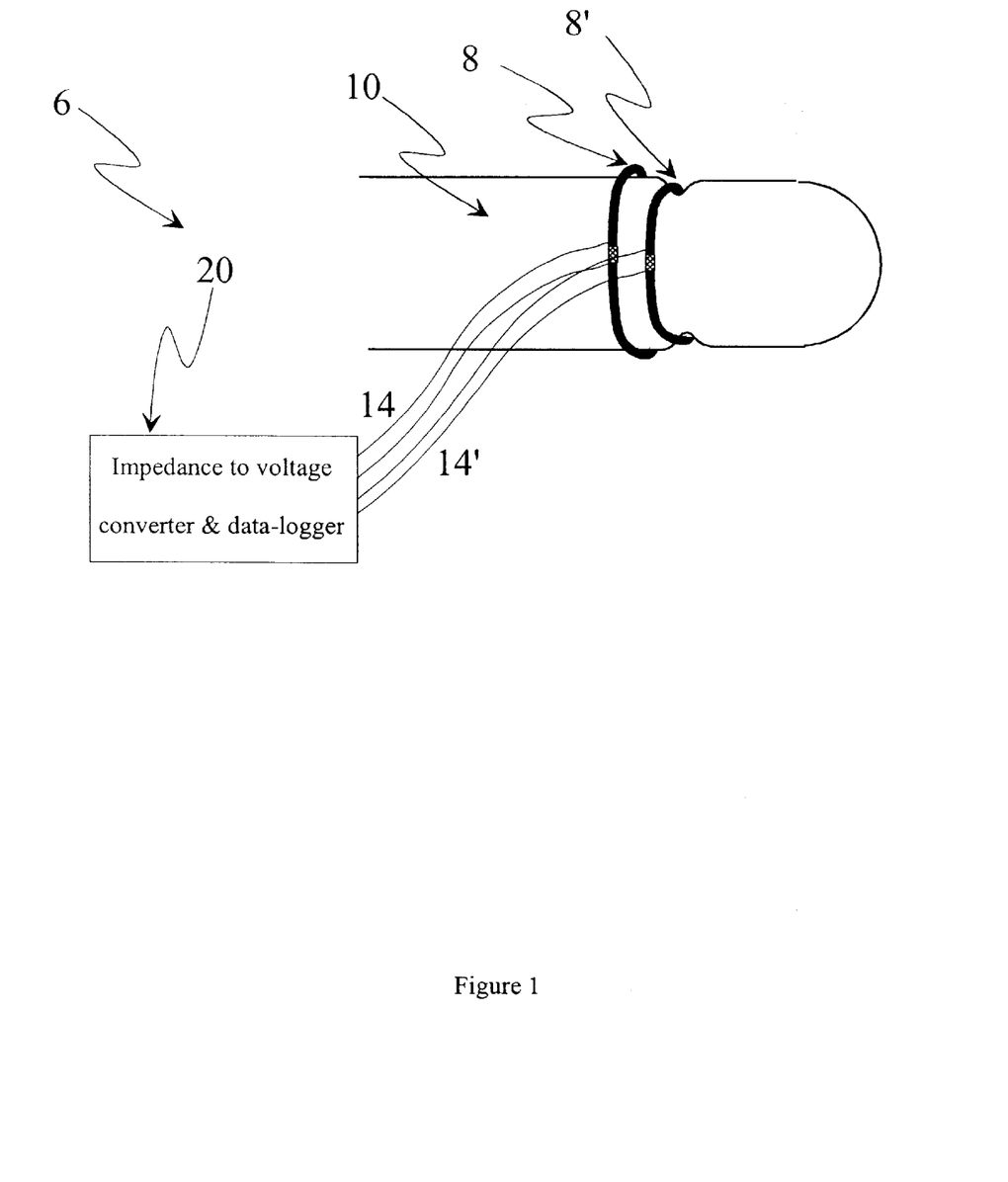
FIG. 1 is a diagram of a first embodiment of a device for the measurement of penile tumescence and rigidity.

Turning now to FIG. 1, a first embodiment of a device 6 for the measurement of penile tumescence and rigidity is shown. In this embodiment, device 6 comprises two sensors 8 and 8' for the measurement of penile tumescence, placed adjacently to each other around the shaft of a penis 10. Sensors 8 and 8' are of different elasticity to each other, but are otherwise structurally identical. Sensors 8 and 8' are connected to an impedance to voltage converter and data-logger unit 20 via a pair of conductive wires 14 and 14' respectively. Impedance to voltage converter and data-logger unit 20 measures the resistances across sensors 8 and 8', and outputs values for the instantaneously measured resistances. In addition impedance to voltage converter and data-logger unit 20 stores the measured data on a flash memory card. At the completion of the study the output from impedance to voltage converter and data-logger unit 20 is transferred to a computer processor (not shown) via cable (not shown). In an alternative embodiment, the data output from an impedance to voltage converter is transmitted by a radio frequency transmitter (not ,shown) to a bedside radio frequency receiver, where the data is stored on a flash memory device. At the end of the study the data is transferred to a computer processor. A standard telemetry system is suitable for use as the radio frequency transmitter and receiver.

The computer processor then analyzes the data received along with the values for the unstressed length, cross-sectional area and resistivity of sensors 8 and 8', so as to calculate indices of penile tumescence and rigidity. These calculations are performed using standard software algorithms which will be well known to one familiar with the art. The computer uses calibration polynomials to obtain the circumference from the input signals, and generates graphs of tumescence as a function of time and a rigidity index as a function of time. The rigidity index is calculated as the ratio of the circumferences of sensors 8 and 8', such that an index of 1.0 indicates full rigidity. The resultant output can be either displayed on a monitor, printed, or stored for later retrieval and display.

Figure 2:
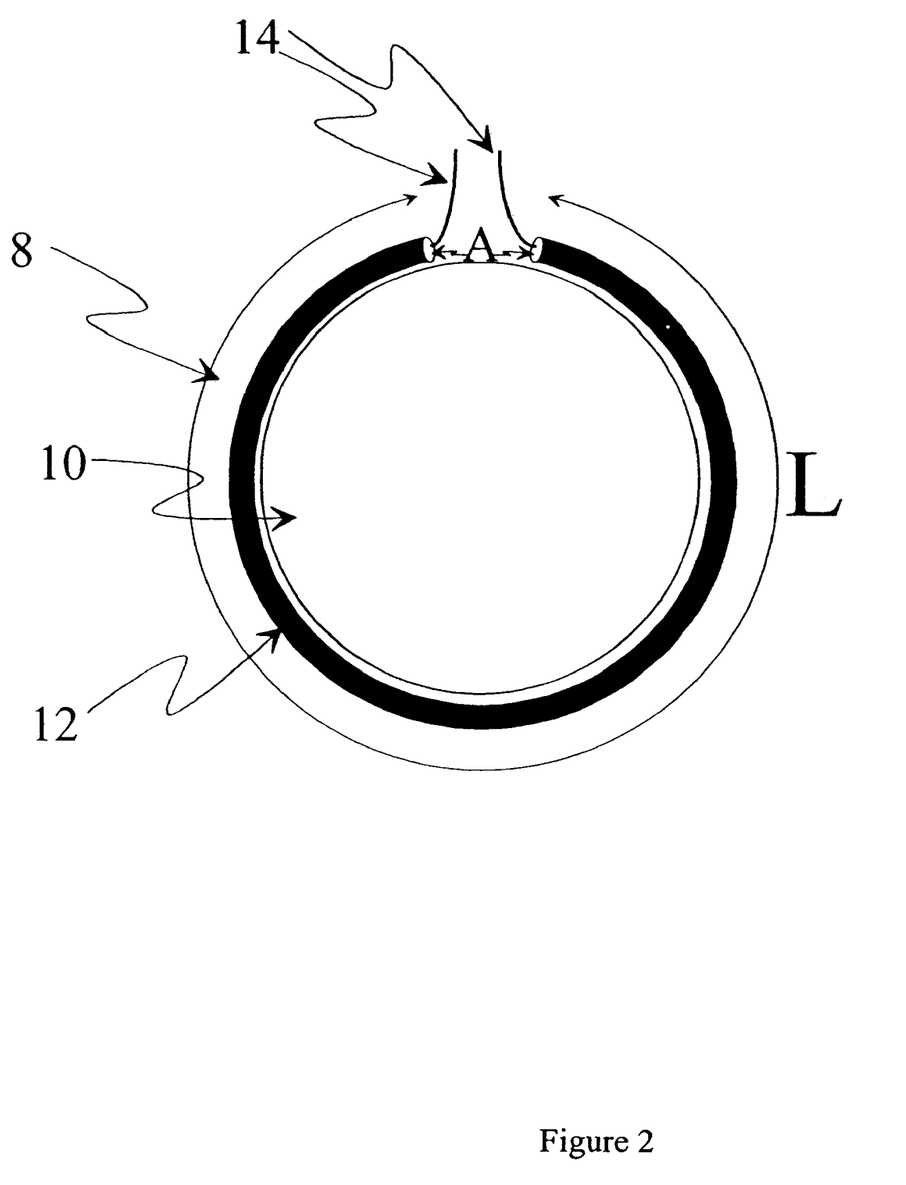
FIG. 2 is a diagram of a sensor for the measurement of penile tumescence.

Turning now to FIG. 2, a preferred embodiment of sensor 8 for the measurement of penile tumescence is shown. Sensor 8 surrounds the circumference of penis 10, which is shown in cross-section. Sensor 8 comprises an elastic band 12 and two conductive wires 14, which enter elastic band 12 in close proximity to each other. The two ends of conductive wires 14 entering elastic band 12 are connected to each other by an electrically conductive material (not shown) running, throughout the full length of, and fully enclosed within, the long axis of elastic band 12. Thus, conductive wires 14 and the electrically conductive material within elastic band 12 form a loop around penis 10. Elastic band 12 may be made of conductive silicone coated with nonconductive silicone, or any other elastic material that is electrically non-conductive. Silicone combined with an electrically conductive material such as carbon or graphite that makes the silicone compound conductive is suitable for use as the electrically conductive material within elastic band 12. For purposes of illustration, conductive wires 14 are shown entering and leaving elastic band 12 through a non-conductive "gap" in elastic band 12, however it should be understood that elastic band 12 is a physically complete ring into which conductive wires 14 insert, with a non-conductive area between the points of insertion of each of the wires of conductive wires 14.

As penis 10 enlarges due to tumescence, the circumference of elastic band 12 increases. The principle of operation of sensor 8 is that a passively measurable property of sensor 8 varies with elongation of elastic band 12. In this embodiment of the current invention, the varying property is the electrical resistance of the electrically conductive material within elastic band 12, although it will be understood that the inductance or capacitance of the electrically conductive material within elastic band 12 may also be used without departing from the spirit of the current invention.

The electrical resistance (R) of sensor 8 is $$R = \frac{\rho L}{A},$$

where $\rho$ is resistivity, L is the length of elastic band 12, and A is the cross-sectional area of elastic band 12. An increase in circumference of penis 10 (i.e. an increase in L) causes a decrease in the cross-sectional area A of elastic band 12, according to the material's Poisson's ratio that relates strain in orthogonal axes. Stretching elastic band 12 nay also increase its resistivity ($\rho$). These effects together result in an increase in electrical resistance across sensor 8 in response to an increase in circumference of penis 10.

Placing an electrically conductive band on a biological tissue may cause errors in measurements of resistance due to the electrical conductivity of the biological tissue itself, which may function as a resistance in parallel to the sensor resistance. Therefore, the electrically conductive material within elastic band 12 must be electrically isolated from penis 10. This is achieved by embedding the conductive material in a nonconductive rubber band or silicone cover, as described above.

As the circumference of penis 10 increases with the development of tumescence, sensor 8 is stretched, thus inducing a change in the electrical resistance of sensor 8. The instantaneous resistance across sensor 8 is measured by impedance to voltage converter and data-logger unit 20. A computer processor then uses this measured resistance to calculate the new length of sensor 8 (which correlates with the circumference of penis 10), using the principles detailed above. Chronological data describing a change in circumference of penis 10 indicates that tumescence has occurred.

Sensor 8' is identical to sensor 8 in all respects, except that the elasticity factor (which is the reciprocal of the compliance) of elastic band 12 is greater in sensor 8' than in sensor 8. In the unstressed state, the circumferences of sensors 8 and 8' are identical, and are set to match the circumference of penis 10.

Thus, in the first embodiment of device 6, each of two sensors 8 and 8' measure penile circumference simultaneously. The circumference of sensor 8, being the more compliant of the two sensors 8 and 8', will approximate the true circumference of penis 10 most closely, and is thus used to describe the status of penile tumescence.

Penile rigidity is described by comparing the simultaneously measured circumferences of sensors 8 and 8'. Sensors 8 and 8', being of different elasticity to each other, will be of different circumferences to each other as penile tumescence progresses, since the centripetal pressures they each apply to the penis are different. The difference between the circumferences of the two sensors is proportional to the rigidity (i.e. the corporeal pressure inside) of the penis. When penis 10 is flaccid, sensors 8 and 8' will be at the same unstressed state and thus have identical circumferences. As corporeal volume increases, the more compliant sensor will increase in size more than will the less compliant of sensors 8 and 8'. However, when full penile rigidity is reached, sensors 8 and 8' will be of almost identical circumference again, as the high penile corporeal pressure will far exceed the centripetal force exerted by both sensor 8 and sensor 8'.

Figure 3:
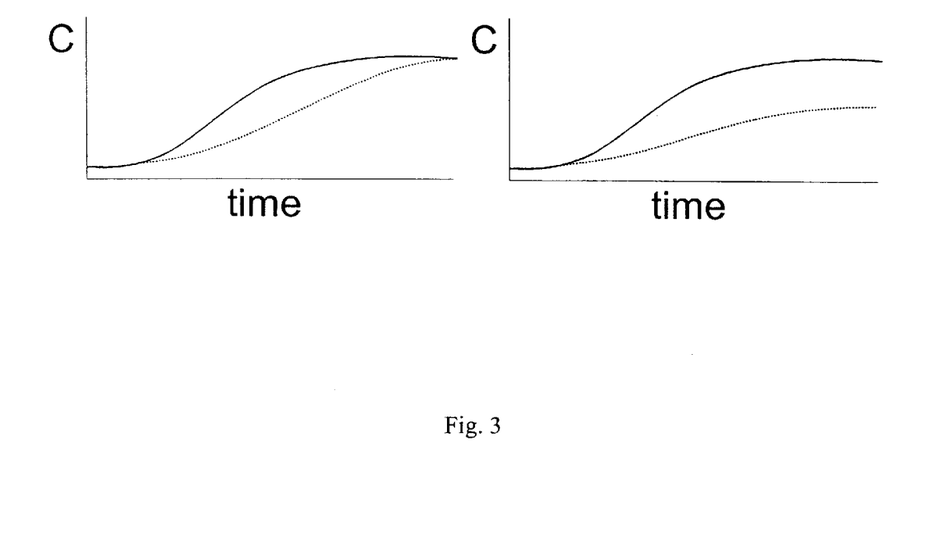
FIG. 3 is a graph showing the changes in circumference of two adjacent tumescence sensors of differing elasticities, during two studies of the development of penile erection.

FIG. 3 is a graph depicting the changes in circumference of sensors 8 and 8' that occur during the course of development of a penile erection. The two panels in FIG. 3 show the findings in two different patients with different degrees of penile rigidity, but with similar penile tumescence. The continuous line represents the circumference of the more compliant sensor (sensor 8) and the dashed line represents the circumference of the stiffer sensor (sensor 8'). The panel on the left shows that a high level of rigidity had been reached, as the two lines eventually coincide. The panel on the right shows that a similar level of tumescence had been obtained (the more compliant sensor traced an identical curve in both patients), but with a lower level of final rigidity (as the two lines do not coincide). The ratio of the circumferences of the two bands can be used as an index of rigidity where a value of 1 represents the highest degree of rigidity and decreasing values represent lesser degrees of, or a failure to achieve, rigidity. Such a ratio is hereinafter also referred to as a "comparator".

In an alternative embodiment of sensor 8, sensor 8 is fabricated from an incompressible conductive liquid (such as saline solution) or gel (such as that used for ultrasonic or ECG electrode coupling) enclosed within a silicone or similar elastic tube, instead of an electrically conductive solid material enclosed within an elastic band as described above. This alternative embodiment of sensor 8 is thus similar to the device described in U.S. Pat. No. 4,103,678 to Karacan, except that the fluid used in the current invention is non-toxic. The elastic tube prevents evaporation of the fluid through its wall. Conductive wires 14 are attached to the conductive fluid, each wire being attached to the fluid on either side of a non-conductive partition dividing the tube in its short axis. In this circumstance, the volume of the fluid is constant and is equal to the product of A (the cross-sectional area) and L (the length) of the elastic tube. Thus, A can be expressed as the ratio V/L, where V is the fluid volume. Using the principles described above for calculating electrical resistance, and substituting A with the ratio V/L, results in the relationship $$R = \frac{\rho L^2}{V},$$

where R is a function of L.

In a second embodiment of device 6, a single sensor, of identical structure to that described above for sensor 8, is used for the measurement of both penile tumescence and penile rigidity. In this embodiment, tumescence is measured in the same manner as described above with regard to FIGS. 2 and 3, however penile rigidity is measured by analyzing volumetric pulsation characteristics (that is, plethysmographic characteristics) of penis 10 as detected by sensor 8. In this embodiment of device 6, the sensor may be identical to either of the embodiments of sensor 8 described above with reference to FIG. 2. In the event that the sensor of this embodiment of device 6 is structured as an elastic band containing an electrically conductive material, the elastic material used is of very low viscoelasticity (time constant less than 0.4 seconds), such that the sensor is capable of responding to rapid pulsatory changes in penile circumference with high fidelity. Alternatively, the fluid-filled sensor described above as an alternative embodiment of sensor 8 may be used, as the fluidic structure of this sensor renders it capable of responding to rapid pulsatory changes in penile circumference with high fidelity.

Figure 4:
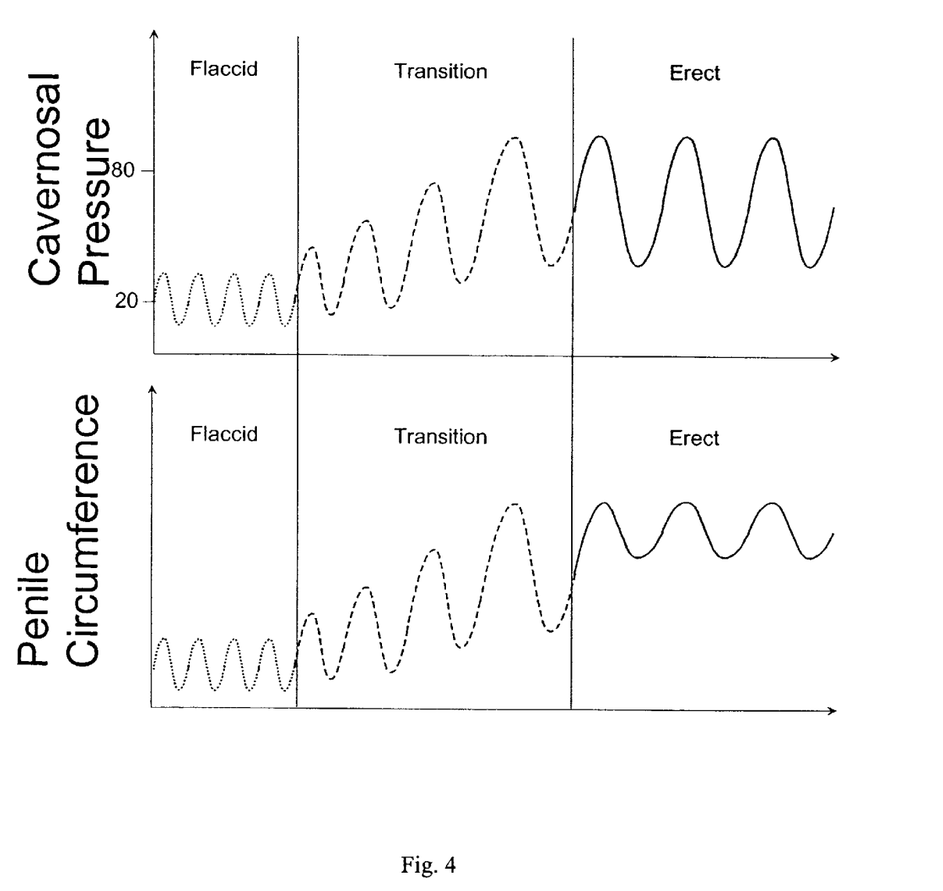
FIG. 4 is a graph depicting the changes which occur in penile pressure and circumference as a penis progresses from a flaccid to an erect state.

FIG. 4 depicts the penile pulse-pressure waveform (in the upper graph) and the corresponding pulsatile changes in penile volume (in the lower graph) which occur during the course of penile erection. Normally, in the flaccid stale, the mean pressure within the penile erectile tissue is approximately 20 mmHg. This pressure is, in fact, the blood pressure within the penile corporeal capillary bed, and as such, is determined by the state of arterial and venous vascular tone on either side of the capillary system. Systolic and diastolic blood pressure changes occur within this capillary system, resulting in a measurable plethysmographic waveform of definable amplitude. As penile arterial resistance is high and venous resistance low during the flaccid state, the plethysmographic pulse amplitude is low. This is shown in FIG. 4 by the dotted tracing in the leftmost section. During the transition from the flaccid to the erect state, arterial resistance decreases while venous resistance increases, thereby raising mean pressure to a near systemic level of approximately 80 mmHg, and increasing the pulse-pressure amplitude, as shown in the middle section of FIG. 4. During the initial phases of tumescence the penile elasticity factor $$\left(\text{defined as } \frac{dP}{dV}\right)$$

is low, and thus the compliant tissue undergoes volumetric pulsation in consonance with pulsation of the pressure waveform. However, as the penile tissue becomes rigid, the penile elasticity factor increases. As a result, the amplitude of these pulsatile changes in penile volume induced by pressure pulsations (i.e. the plethysmographic waveform), decreases. The rigid penis is thus less pulsatile, and is characterized by a higher mean pressure, but diminished plethysmographic pulse amplitude, than that of the tumescent but non-rigid penis.

In this second embodiment of device 6, the single sensor is connected to an impedance to voltage converter and data-logger unit and a computer processor, as described above with regard to the first embodiment of the current invention. The computer processor performs the same functions as described above with regard to the first embodiment, and in addition analyzes the acquired waveform amplitude so as to detect a decrease of the waveform amplitude combined with an increase in penile circumference. Such a finding indicates the occurrence of penile rigidity. The ratio between the amplitude of the pressure waveform prior to the phase of rigidity and that of the pressure waveform during the phase of rigidity (that is., the ratio of the pulse amplitude divided by the largest pulse amplitude that was measured during the duration of the study until that point in time) is an index of rigidity. This ratio is hereinafter also referred to as a "comparator". The mean magnitude of the plethysmographic signal, which is achieved by filtering out the pulsatile component of the signal, is an index of tumescence.

Impedance to voltage converter and data-logger unit 20 measures the resistance across the two ends of conductive wires 14 using) a resistor bridge configuration with sinusoidal excitation voltage. The impedance of the electrode-liquid interface is high at DC and low frequencies and is significantly reduced at higher frequencies. At frequencies of 50 KHz and higher this impedance becomes purely resistive and independent of the frequency since the capacitive element is neutralized. At these frequencies the resistance that is related to the circumference is measured with minimal effects of the electrode impedance.

Figure 5:
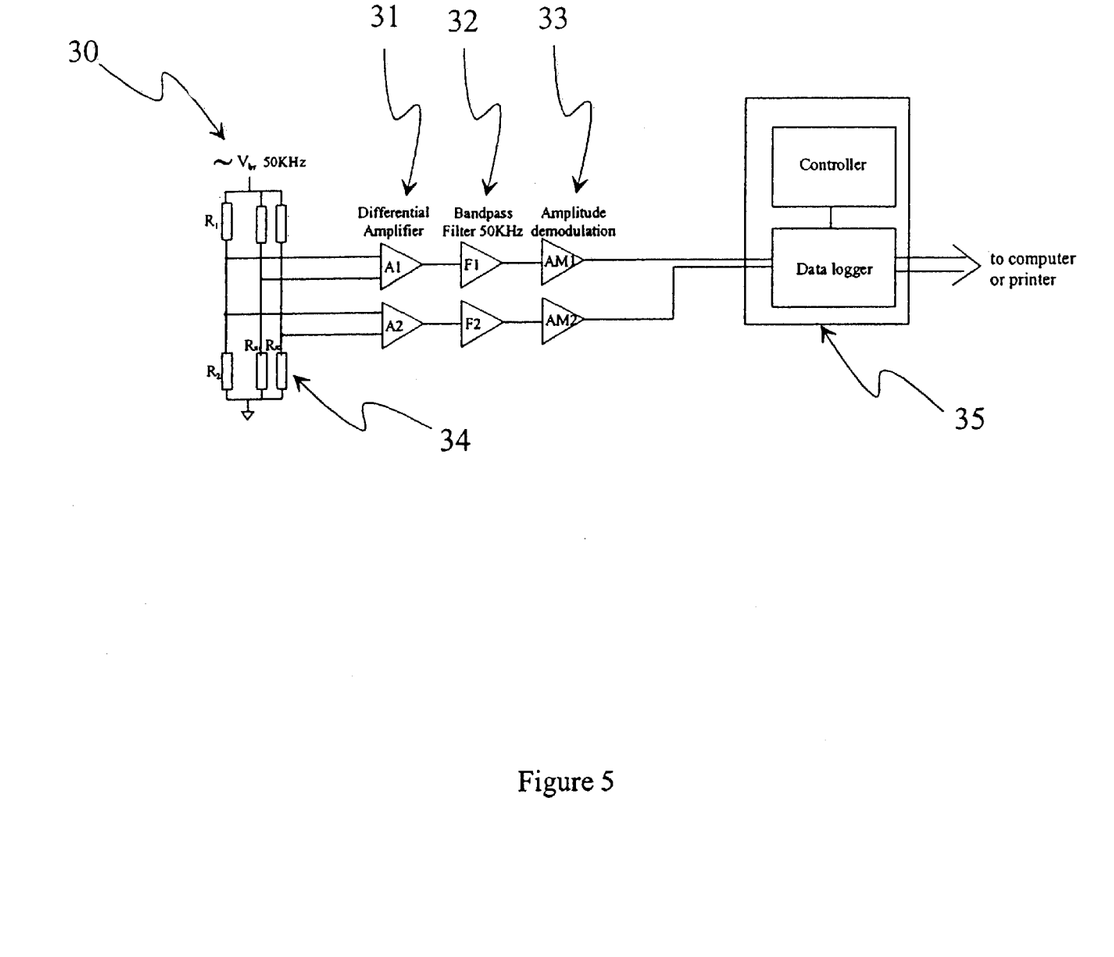
FIG. 5 is a diagram of the electrical circuitry of an impedance to voltage converter and data-logger unit.

FIG. 5 shows the electrical circuitry of impedance to voltage converter and data-logger unit 20, which is an electrical circuit for the measurement of impedance at a specific frequency. The impedance of an electrode-liquid interface is high at DC and low frequencies and is significantly reduced at higher frequencies. At frequencies of 50 KHz and higher this impedance becomes purely resistive and independent of the frequency since the capacitive element is neutralized. At these frequencies the resistance that is related to the circumference is measured with minimal effects of the electrode impedance. Thus, when sensor 8 is a fluid-filled elastic tube, the impedance of the interface between the electrode and the fluid is eliminated. In the circuit depicted in FIG. 5, R1 and R2 are resistors used to generate a reference voltage for the measurement of the resistance of channels $Rs_1$ and $Rs_2$ 34. Channels $Rs_1$ and $Rs_2$ 34 in the circuit represent sensors 8 and 8'. The input signals received from sensors 8 and 8' first pass through a differential amplifier 31, a bandpass filter 31 (to reduce noise), a demodulator 33 (that supplies the envelope of the measured signal and eliminates the 50 KHz signal). The output signal, which depicts the circumferences of sensors 8 and 8', is stored in a flash memory device in a data-logger 35, and later transferred to a computer via RS232 or by other means. A flash memory device suitable for use in data-logger 35 is A-ENGINE-P (TERN INC., Davis, Calif.).

Figure 6:
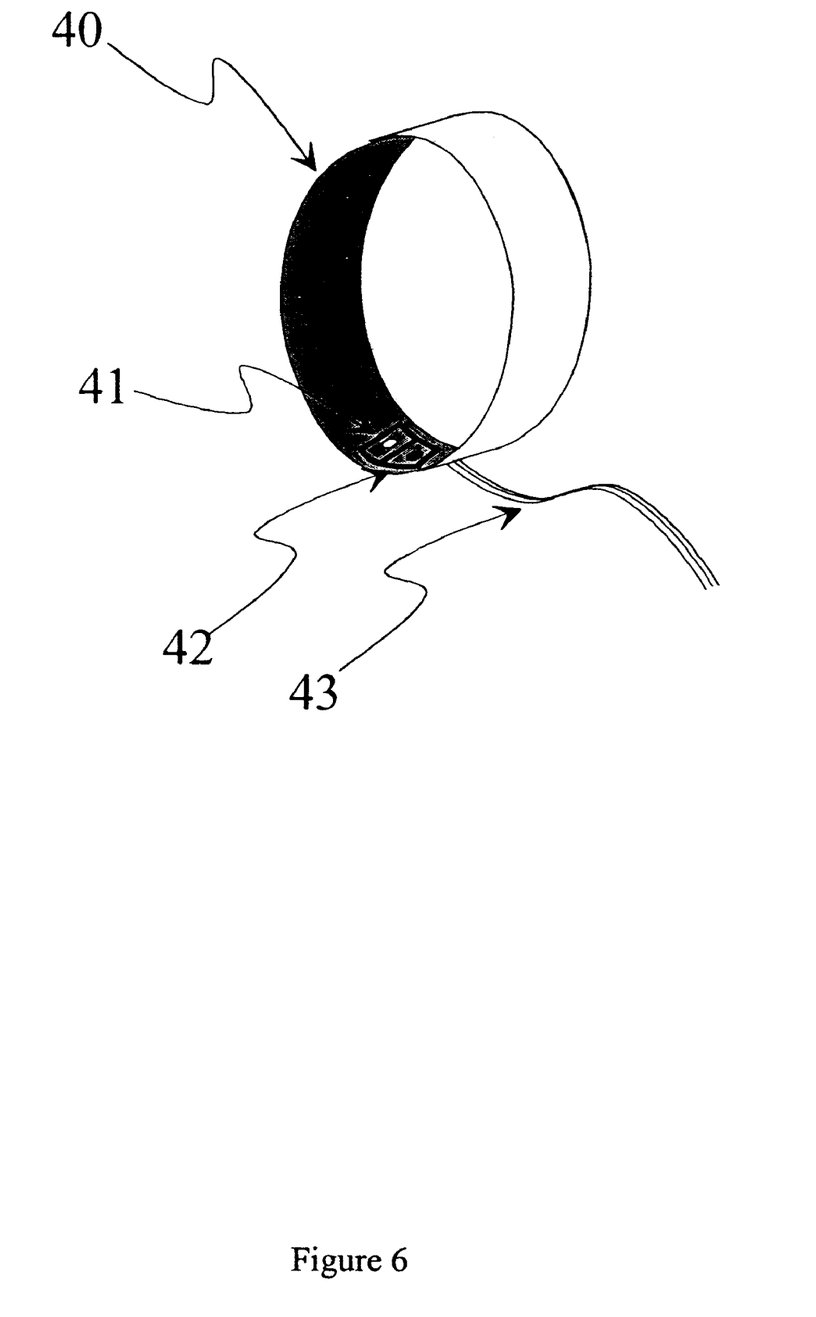
FIG. 6 is a diagram of a reflective photoplethysmographic sensor suitable for use in the current invention.

FIG. 6 depicts a third embodiment of the current invention, in which either a reflective or transmissive photoplethysmograph 40 is attached to penis 10 for use as a sensor, instead of the single sensor 8 described above with regard to the second embodiment of the current invention. Photoplethysmograph 40 is a standard photoplethysmograph such as a TSD100B photoplethysmograph (Biopac Systems, Ltd. Santa Barbara, Calif.). Photoplethysmograph 40 transmits a light ray into penis 10 from a location 41 on photoplethysmograph 40, and measures the reflected light received by a light sensor at a different location 42 on photoplethysmograph 40. The electrical circuit used to convert the reflected light intensity to an electrical signal is well described in the art (Medical Instrumentation—Application and design, editor: J. G. Webster, Houghton Mifflin Company Boston, 1978, page 429). Changes in the amount of blood in penis 10 affect the absorption of the light transmitted into penis 10, and therefore the intensity of the received signal at location 42. The acquired photoplethysmographic signal is input directly into a data logger or RF transceiver unit (not shown) via a connecting cable 43, and subsequently a computer processor, as described above with regard to the first and second embodiments of the current invention. In a manner similar to that described above with regard to the second embodiment of the current invention, the computer processor then analyzes the photoplethysmographic signal, and generates indices of tumescence from the mean intensity of the photoplethysmographic signal. The value for mean intensity of the photoplethysmographic signal is the trend of both the low frequency components of the signal (i.e. those frequencies having a time constant of approximately three seconds or greater), and the D.C. (direct current) components of the signal (i.e. the components of the signal having a frequency of zero). Indices of penile rigidity are generated from the amplitude of the signal using the same method as described above with regard to the second embodiment of device 6.

To avoid the effects of blood oxygen saturation on the level of the reflected light signal, a wavelength that is close to the isobestic wavelength of oxygenated and deoxygenated hemoglobin (i.e. 804 nm.) is required. As a large depth of penetration is desired, a somewhat larger wavelength (840 nm or 880 nm) is used. The strength of the signal received by reflective photoplethysmograph 40 also depends on the distance between the light emitter and receiver of photoplethysmograph 40. Photoplethysmograph 40 is therefore placed on penis 10 and held in place gently using surgical tape, or a similar material, in a manner that does not limit penile elasticity, volume changes or blood flow, and which maximizes The proximity of the light receiver and emitter of photoplethysmograph 40.

There has therefore been described a single device capable of automatically measuring both penile tumescence and penile rigidity by passive means. As the electronic components of the device are very small and lightweight, the device is comfortable for the user to wear, and does not disturb the users sleep. Furthermore, as the means used to measure penile tumescence and rigidity are completely passive, with no active pressure generated against the penis, the device does not cause pain or discomfort to the user. As the constituents and components of the device are all inert and non-toxic, the device is safe to wear, incurring no risk of exposure of the penis to noxious substances. Furthermore, as the passive sensor of the device, which comes in contact with the user's penis, is inexpensive to manufacture, the sensor is disposable and therefore does not undergo resterilization for multiple use by many patients.

What is claimed is:

1. A method for measuring the rigidity of a penis, comprising a) positioning a first circular sensor and a second circular sensor around the penis, said first and second circular sensors each being of different elasticity to each other;

b) measuring a circumference of said first circular sensor and a circumference of said second circular sensor; and c) calculating a comparator of said measured circumferences of said first and second circular sensors.

2. The method of claim 1, wherein said circular sensors include an electrically conductive material within an elastic band.

3. The method of claim 1, wherein said circular sensors include an electrically conductive fluid contained within an elastic tube.

4. The method of claim 3, wherein said electrically conductive fluid is selected from the group consisting of coupling gel and normal saline.

5. The method of claim 1, wherein said measuring is achieved by sensing a change in electrical resistance across said circular sensors.

6. The method of claim 1, wherein said comparator is a ratio between said measured circumferences.

7. A method for measuring erectile function of a penis, comprising a) sensing a plethysmographic signal from the penis, said plethysmographic signal depicting pulsatory changes in the penile volume over time; and b) measuring a mean intensity of said sensed plethysmographic signal,
wherein said sensed plethysmographic signal is determined exclusively passively and wherein said sensed plethysmographic signal is used for measurement of penile tumescence and penile rigidity.

8. The method of claim 7, wherein said sensing is achieved by detecting a change in electrical resistance across an electrically conductive material within an elastic band.

9. The method of claim 7, wherein said sensing is achieved by detecting a change in electrical resistance across an electrically conductive fluid contained within an elastic tube.

10. The method of claim 9, wherein said electrically conductive fluid is selected from the group consisting of coupling gel and normal saline.

11. The method of claim 7, wherein said sensing is achieved by photoplethysmography.

12. The method of claim 7, further comprising c) measuring an amplitude of said sensed plethysmographic signal over time; and d) detecting an increase over time in said measured mean intensity and a decrease over time in said measured amplitude of said plethysmographic signal.

13. A system for measuring rigidity of a penis, comprising:
   a) a first circular sensor, operative to increase in diameter in response to an increase in diameter of the penis;
   b) a second circular sensor, operative to increase in diameter in response to an increase in diameter of the penis, said second circular sensor being of different elasticity to said first circular sensor;
   c) a mechanism for measuring a circumference of each of said circular sensors; and
   d) a processor for calculating a comparator of said measured circumferences of each of said circular sensors.

14. The system of claim 13, wherein said circular sensors include an electrically conductive material within an elastic band.

15. The system of claim 13, wherein said circular sensors include an electrically conductive fluid contained within an elastic tube.

16. The system of claim 15, wherein said electrically conductive fluid is selected from the group consisting of coupling gel and normal saline.

17. The system of claim 13, wherein said mechanism includes an impedence to voltage converter operative to measure an electrical resistance across said circular sensor.

18. The method of claim 13, wherein said comparator is a ratio between said measured circumferences.

19. A system for measuring erectile function of a penis, comprising
   a) a plethysmographic sensor, operable to sense a plethysmographic signal from the penis; and
   b) a processor, operable to process said sensed plethysmographic signal so as to describe a change in mean signal intensity signal,
      wherein said sensed plethysmographic signal is determined exclusively passively and wherein said sensed plethysmographic signal is used for measurement of penile tumescence and penile rigidity.

20. The system of claim 19, wherein said plethysmographic sensor includes an electrically conductive material within an elastic band.

21. The system of claim 19, wherein said plethysmographic sensor includes an electrically conductive fluid contained within an elastic tube.

22. The system of claim 21, wherein said electrically conductive fluid is selected from the group consisting of coupling gel and normal saline.

23. The system of claim 19, wherein said plethysmographic sensor includes a photoplethysmograph.

24. The system of claim 19, wherein said processor is operable to further process said sensed plethysmographic signal so as to describe a change in signal amplitude.

* * * * *